(12) United States Patent
Stocker et al.

(10) Patent No.: US 7,166,636 B2
(45) Date of Patent: Jan. 23, 2007

(54) INDOLE-AMID DERIVATIVES WHICH POSSESS GLYCOGEN PHOSPHORYLASE INHIBITORY ACTIVITY

(75) Inventors: Andrew Stocker, Cheshire (GB); Paul Whittamore, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 75 days.

(21) Appl. No.: 10/506,729

(22) PCT Filed: Mar. 4, 2003

(86) PCT No.: PCT/GB03/00924

§ 371 (c)(1),
(2), (4) Date: Sep. 3, 2004

(87) PCT Pub. No.: WO03/074517

PCT Pub. Date: Sep. 12, 2003

(65) Prior Publication Data
US 2005/0130963 A1 Jun. 16, 2005

(30) Foreign Application Priority Data
Mar. 6, 2002 (GB) .................................. 0205175.3

(51) Int. Cl.
C07D 209/12 (2006.01)
C07D 209/14 (2006.01)
A61K 31/404 (2006.01)

(52) U.S. Cl. ...................................... 514/419; 548/492

(58) Field of Classification Search ................ 548/492; 514/419
See application file for complete search history.

(56) References Cited

U.S. PATENT DOCUMENTS

| | | | |
|---|---|---|---|
| 3,706,810 A | 12/1972 | Brabander et al. | |
| 4,599,198 A | 7/1986 | Hoover | |
| 4,668,769 A | 5/1987 | Hoover | |
| 4,720,503 A | 1/1988 | Witzel | |
| 4,751,231 A | 6/1988 | Halczenko | |
| 4,786,641 A | 11/1988 | Goldmann | |
| 4,794,120 A | 12/1988 | Manoury | |
| 5,863,903 A | 1/1999 | Lundgren | |
| 5,998,463 A | 12/1999 | Hulin | |
| 6,277,877 B1* | 8/2001 | Hoover et al. ............... | 514/415 |
| 2004/0002495 A1 | 1/2004 | Sher | |
| 2004/0142938 A1 | 7/2004 | Sher et al. | |
| 2004/0220229 A1 | 11/2004 | Bussolotti et al. | |
| 2004/0266768 A1 | 12/2004 | Schoenafinger et al. | |

FOREIGN PATENT DOCUMENTS

| | | |
|---|---|---|
| DE | 200740 | 6/1983 |
| DE | 4445968 | 6/1996 |
| EP | 697403 | 2/1996 |
| EP | 0846464 | 6/1998 |
| EP | 0884050 | 12/1998 |
| EP | 0978279 | 2/2000 |
| EP | 1149580 | 2/2001 |
| EP | 1177791 | 7/2001 |
| EP | 1125580 | 8/2001 |
| EP | 1134213 | 9/2001 |
| EP | 1136071 | 9/2001 |
| EP | 1 338 594 A1 | 8/2003 |
| EP | 1 340 500 A1 | 9/2003 |

(Continued)

OTHER PUBLICATIONS

Birch, A., et al., "Novel Thienopyrrole Glycogen Phosphorylase Inhibitors: In Vitro SAR and Crystallographic Studies," Poster, AstraZeneca UK, CVGI Research, Mereside, Alderley Park, Macclesfield, Cheshire.

(Continued)

Primary Examiner—Kamal A. Saeed
Assistant Examiner—Michael Barker

(57) ABSTRACT

Heterocyclic amides of formula (1)

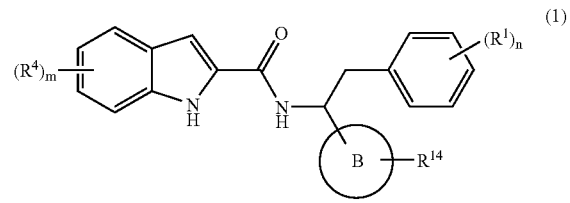

wherein:
m is 0, 1 or 2;
n is 0, 1 or 2;
B is phenyl or heterocyclyl;
$R^1$ is selected from for example halo, nitro, cyano, hydroxy, carboxy;
$R^2$ and $R^3$ are independently selected from, for example, $C_{5-7}$cycloalkyl, cyano($C_{1-4}$)alkyl, $C_{1-4}$alkyl (optionally substituted with 1 or 2 $R^8$ groups), —$OR^8$ and $R^8$;
$R^4$ is independently selected from for example hydrogen, halo, nitro, cyano, hydroxy, $C_{1-4}$alkyl, and $C_{1-4}$alkanoyl;
$R^8$ is selected from for example hydroxy, heterocyclyl, aryl, —COCOOR$^9$, —C(O)N(R$^9$)(R$^{10}$), (R$^9$)(R$^{10}$)N— and —COOR$^9$;
$R^9$ and $R^{10}$ are selected from for example hydrogen, hydroxy, $C_{1-4}$alkyl (optionally substituted by 1 or 2 $R^{13}$);
$R^{13}$ is selected from for example, hydroxy, $C_{1-4}$alkoxy, heterocyclyl and $C_{1-4}$alkanoyl;
$R^{14}$ is selected from for example, hydrogen, halo, $C_{1-4}$alkyl, $C_{5-7}$cycloalkyl, $C_{1-4}$alkoxy, cyano, cyano($C_{1-4}$)alkyl, —COR$^3$, (R$^2$)(R$^3$)NCO—, and (R$^2$)(R$^3$)NSO$_2$—;
or a pharmaceutically acceptable salt or pro-drug thereof; possess glycogen phosphorylase inhibitory activity and accordingly have value in the treatment of disease states associated with increased glycogen phosphorylase activity. Processes for the manufacture of said heterocyclic amide derivatives and pharmaceutical compositions containing them are described.

6 Claims, No Drawings

FOREIGN PATENT DOCUMENTS

| | | |
|---|---|---|
| EP | 1088824 | 1/2004 |
| EP | 1145717 | 5/2004 |
| ES | 2081747 | 3/1996 |
| JP | 021247565 | 5/1990 |
| JP | 04179949 | 6/1992 |
| JP | 2001 089368 | 4/2001 |
| JP | 2001 206856 | 7/2001 |
| JP | 2001247565 A | 9/2001 |
| JP | 2004196702 A | 7/2004 |
| WO | WO-93/25574 | 12/1993 |
| WO | WO-95/24391 | 9/1995 |
| WO | WO-96/39384 | 12/1996 |
| WO | WO-96/39385 | 12/1996 |
| WO | WO-97/09040 | 3/1997 |
| WO | WO-97/31901 | 9/1997 |
| WO | WO-97/45425 | 12/1997 |
| WO | WO 9745425 A1 * | 12/1997 |
| WO | WO-98/27108 | 6/1998 |
| WO | WO-98/40353 | 9/1998 |
| WO | WO-98/50359 | 11/1998 |
| WO | WO-99/26659 | 6/1999 |
| WO | WO-99/36393 | 7/1999 |
| WO | WO-00/42213 | 7/2000 |
| WO | WO-00/47206 | 8/2000 |
| WO | WO-01/05954 | 1/2001 |
| WO | WO-01/23347 | 4/2001 |
| WO | 01/32622 A1 | 5/2001 |
| WO | WO-01/32654 | 5/2001 |
| WO | WO-01/52825 | 7/2001 |
| WO | WO-01/68055 | 9/2001 |
| WO | WO-01/68092 | 9/2001 |
| WO | WO-01/68603 | 9/2001 |
| WO | WO-01/94300 | 12/2001 |
| WO | WO-01/96311 | 12/2001 |
| WO | WO-01/96347 | 12/2001 |
| WO | 02/20530 A1 | 3/2002 |
| WO | WO-02/26714 | 4/2002 |
| WO | WO-02/34718 | 5/2002 |
| WO | WO 200234718 A1 * | 5/2002 |
| WO | WO-02/080644 | 10/2002 |
| WO | WO-02/096864 | 12/2002 |
| WO | WO-02/098348 | 12/2002 |
| WO | WO-03/037864 | 5/2003 |
| WO | 03/045920 A1 | 6/2003 |
| WO | 03/072570 A1 | 9/2003 |
| WO | 03/074484 A1 | 9/2003 |
| WO | 03/074485 A2 | 9/2003 |
| WO | 03/074513 A2 | 9/2003 |
| WO | 03/074531 A1 | 9/2003 |
| WO | 03/074532 A1 | 9/2003 |
| WO | 03/091213 A1 | 11/2003 |
| WO | 2004/031193 A1 | 4/2004 |
| WO | 2004/031194 A1 | 4/2004 |
| WO | 2004/041780 A2 | 5/2004 |
| WO | 2004/092158 A1 | 10/2004 |
| WO | 2004/104001 A2 | 12/2004 |
| WO | 2004113345 A1 | 12/2004 |
| WO | 2005/013975 A1 | 2/2005 |
| WO | 2005/013981 A1 | 2/2005 |
| WO | 2005/018637 A1 | 3/2005 |
| WO | 2005/019172 A1 | 3/2005 |
| WO | 2005/020985 A1 | 3/2005 |
| WO | 2005/020986 A1 | 3/2005 |
| WO | 2005/020987 A1 | 3/2005 |

OTHER PUBLICATIONS

Crochet, R.A., et al., "Synthesis of Substituted Thieno[2,3-b] pyrroles," vol. 11, 143-150 (Apr. 1974).

Freeman, S., et al., "Effect of Glucose on Rat and Human Liver Glycogen Phosphorylasea Activity and Potency of a Glycogen Phosphoylase Inhibitor," Diabetes, 52, Supp., 1470-P, A340.

Hartman, G.D., et al., "The Synthesis of 5-Alkylaminomethylthieno[2,3-b] Pyrrole-5-Sulfonamides," Heterocycles, 29(10):1943-1949 (1989).

Hoover, D.J., et al., "Indote-2-carboxamide Inhibitors of Human Liver Glycogen Phosphorylase," J. Med. Chem., 41:2934-2938 (1998).

Hudson, S., et al., "The effect of a glycogen phosphorylase inhibitor upon muscle fatigue in anaesthetised rats," J. Physiol., 539:52-53 (2002).

Jakobsen, P., et al., "Iminosugars: Potential Inhibitors of Liver Glycogen Phosphorylase.," Bioorganic Med. Chem., 9:733-744 (2001).

Martin, W.H., et al., "Discovery of a human liver glycogen phosphorylase inhibitor that lowers blood glucose in vivo," PNAS, 95:1776-1781 (Feb. 1998).

McCormack, J. G., et al., "Pharmacological Approaches to Inhibit Endogenous Glucose Production as a Means of Anti-diabetic Therapy," Curr. Pharmaceutical Design, 7:1451-1474 (2001).

Rath, V.L. et al., "Activation of Human Liver Glycogen Phosphorylase by Alteration of the Secondary Structure and Packing of the Catalytic Core," Mol. Cell, 6:139-148 (Jul. 2000).

Rosauer, K.G., et al., "Novel, 3,4-Dihydroquinolin-2(1H)-one Inhibitors of Human Glycogen Phosphorylase a," Bioorganic & Medicinal Chemistry Letters, 13:4385-4388 (2003).

Soman, G., et al. "Aromatic Compounds as Allosteric Inhibitors of Glycogen Phosphorylase beta," Biochimica et Biophysica Acta, 358:359-362 (1974).

Soman, G., et al., "The Nature of the Binding Site for Aromatic Compounds in Glycogen Phosphorylase beta," Biochem. J., 147:369-371 (1975).

Teague, J., "Mobilisation of Tissue Glycogen Following Inhibition of Glycogen Phosphorylase in fa/fa Rat," Diabetes, 53, Supp. 1, A365, 1521-P.

Treadway, J.L., et al., "Glycogen phosphorlase inhibitors for treatment of type 2 diabetes mellitus," Exp. Opin. Invest. Drugs, 10(3):439-454 (2001).

Turnbull, A., et al., "Pharmacological Inhibition of Glycogen Phosphorylase (GP) Lowers Plasma Glucose in Rat Models of Type 2 Diabetes," Diabetes, 52, Supp., 1485-P, A343.

Venkatarangan, P., et al., "Prediction of Ligand-REceptor Binding Thermodynamics by Free Energy Force Field Three-Dimensional Quantitative Structure-Activity Relationship Analysis: Applications to a Set of Glucose Analogue Inhibitors of Glycogen Phosphorylase," J. Med. Chem., 42:2169-2179 (1999).

Vertigan, H., "Impact of cell glycogen content on modulation of hepatocyte glucose metabolism by pharmacological agents," Diabetes, 47, Supp., 589, A214.

Font, M. et al. "Indoles and pyridazino[4,5-b] indoles as non-nucleoside analog inhibitors of HIV-1 reverse transcripptase", European Journal Med Chem (1995), 30(12), 963-71.

Lin, T. et al. "Effects of Protein Binding and Experimental Disease States on Brain Uptake of Benzodiazepines in Rats", J Pharmacology & Eptl Therapeutics (1990), 253(1), 45-50.

Varnavas, A. et al. "Quinolone Derivatives: Synthesis and Binding Evaluation on Cholecystokinin Receptors", Farmaco (1996), 51(5), 341-350.

Parsons, W H. et al. "Cholecystokinin Antagonists. Synthesis and Biological Evaluation of 3-Substitued Benzolactams", J Med Chem (1989), 32(8), 1681-5.

Vertigan, H. et al. "Impact of cell glycogen content on modulation of hepatocyte glucose metabolism by pharmacological agents", EASD Munich 2004.

Bartlett, J. et al. "In Vitro and In Vivo Profile of Gpi688, a Novel, Potent Inhibitor of Glycogen Phosphorylase", ADA San Diego 2005.

Green, A R. et al. "The Glycogenic Action of Protein Targeting to Glycogen in Hepatocytes Involves Multiple Mechanisms Including Phosphorylase Inactivation and Glycogen Synthase Translocation", J Biol Chem, 279(45), 46474-46482, 2004.

Roberts, P A. et al. "The temporal relationship between glycogen phosphorylase and activation of the pyruvate dehydrogenase complex during adrenaline infusion in resting canine skeletal muscle", J Physiology-London 545(1), 297-304, 2002.

Simpson, I. et al. "Novel Orally Active Amino-indan Inhibitors of Glycogen Phosphorylase", Cambridge Med Chem Conference, Sep. 2005. Poster EOM.

Crochet, R.A., et al., J. Het. Chem., "Synthesis of Substituted Thieno[2,3-b] pyrroles," vol. 11, 143-150 (Apr. 1974).

Teague, J., "Mobilisation of Tissue Glycogen Following Inhibition of Glycogen Phosphorylase in fa/fa Rat," Diabetes, 52, Supp. 2, A365, 1521-P, 2003.

Vertigan, H., "Impact of cell glycogen content on modulation of hepatocyte glucose metabolism by pharmacological agents," Diabetologia, 47, Supp.1, 589, A214, 2004.

Oikonomakos, N.G., et al., Allosteric inhibition of glycogen phosphorylase alpha by the potential antidiabetic drug 3-isopropyl 4-(2-chlorophenyl)-1,4-dihydro-1-ethyl-2-methyl-pyridine-3,5,6-tricarboxylate, Protein Science, 1999, 1930-1945, 8, Cambridge University Press, USA.

* cited by examiner

INDOLE-AMID DERIVATIVES WHICH POSSESS GLYCOGEN PHOSPHORYLASE INHIBITORY ACTIVITY

This application is a national stage filing under 35 U.S.C. 371 of International Application No. PCT/GB03/00924, filed Mar. 4, 2003, which claims priority from United Kingdom Patent Application No. 0205175.3, filed Mar. 6, 2002, the specification of which is incorporated by reference herein. International Application No. PCT/GB03/00924 was published under PCT Article 21(2) in English.

The present invention relates to heterocyclic amide derivatives, pharmaceutically acceptable salts and in vivo hydrolysable esters thereof. These heterocyclic amide derivatives possess glycogen phosphorylase inhibitory activity and accordingly have value in the treatment of disease states associated with increased glycogen phosphorylase activity and thus are potentially useful in methods of treatment of a warm-blooded animal such as man. The invention also relates to processes for the manufacture of said heterocyclic amide derivatives, to pharmaceutical compositions containing them and to their use in the manufacture of medicaments to inhibit glycogen phosphorylase activity in a warm-blooded animal such as man.

The liver is the major organ regulating glycaemia in the post-absorptive state. Additionally, although having a smaller role in the contribution to post-prandial blood glucose levels, the response of the liver to exogenous sources of plasma glucose is key to an ability to maintain euglycaemia. An increased hepatic glucose output (HGO) is considered to play an important role in maintaining the elevated fasting plasma glucose (FPG) levels seen in type 2 diabetics; particularly those with a FPG>140 mg/dl (7.8 mM). (Weyer et al, (1999), J Clin Invest 104: 787–794; Clore & Blackgard (1994), Diabetes 43: 256–262; De Fronzo, R. A., et al, (1992) Diabetes Care 15; 318–355; Reaven, G. M. (1995) Diabetologia 38; 3–13).

Since current oral, anti-diabetic therapies fail to bring FPG levels to within the normal, non-diabetic range and since raised FPG (and glycHbA1c) levels are risk factors for both macro- (Charles, M. A. et al (1996) Lancet 348, 1657–1658; Coutinho, M. et al (1999) Diabetes Care 22; 233–240; Shaw, J. E. et al (2000) Diabetes Care 23, 34–39) and micro-vascular disease (DCCT Research Group (1993) New. Eng. J. Med. 329; 977–986); the reduction and normalisation of elevated FPG levels remains a treatment goal in type 2 DM.

It has been estimated that, after an overnight fast, 74% of HGO was derived from glycogenolysis with the remainder derived from gluconeogenic precursors (Hellerstein et al (1997) Am J Physiol, 272: E163). Glycogen phosphorylase is a key enzyme in the generation by glycogenolysis of glucose-1-phosphate, and hence glucose in liver and also in other tissues such as muscle and neuronal tissue.

Liver glycogen phosphorylase a activity is elevated in diabetic animal models including the db/db mouse and the fa/fa rat (Aiston S et al (2000). Diabetalogia 43, 589–597).

Inhibition of hepatic glycogen phosphorylase with chloroindole inhibitors (CP91149 and CP320626) has been shown to reduce both glucagon stimulated glycogenolysis and glucose output in hepatocytes (Hoover et al (1998) J Med Chem 41, 2934–8; Martin et al (1998) PNAS 95, 1776–81). Additionally, plasma glucose concentration is reduced, in a dose related manner, db/db and ob/ob mice following treatment with these compounds.

Studies in conscious dogs with glucagon challenge in the absence and presence of another glycogen phosphorylase inhibitor, Bay K 3401, also show the potential utility of such agents where there is elevated circulating levels of glucagon, as in both Type 1 and Type 2 diabetes. In the presence of Bay R 3401, hepatic glucose output and arterial plasma glucose following a glucagon challenge were reduced significantly (Shiota et al, (1997), Am J Physiol, 273: E868).

The heterocyclic amides of the present invention possess glycogen phosphorylase inhibitory activity and accordingly are expected to be of use in the treatment of type 2 diabetes, insulin resistance, syndrome X, hyperinsulinaemia, hyperglucagonaemia, cardiac ischaemia and obesity, particularly type 2 diabetes.

According to one aspect of the present invention there is provided a compound of formula (1):

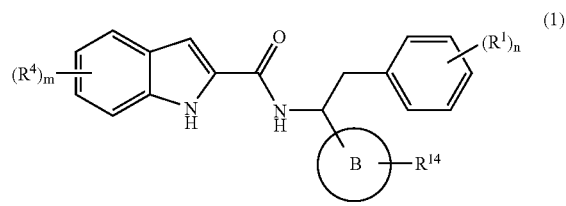

wherein:

n is 0, 1 or 2;

m is 0, 1 or 2;

$R^1$ is independently selected from hydrogen, halo, nitro, cyano, hydroxy, amino, carboxy, carbamoyl, N-$C_{1-4}$alkylcarbamoyl, N,N-($C_{1-4}$alkyl)$_2$carbamoyl, sulphamoyl, N-$C_{1-4}$alkylsulphamoyl, N,N-($C_{1-4}$alkyl)$_2$sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, hydroxy$C_{1-4}$alkyl, fluoromethyl, difluoromethyl, trifluoromethyl, trifluoromethoxy and groups of the formula A or A':

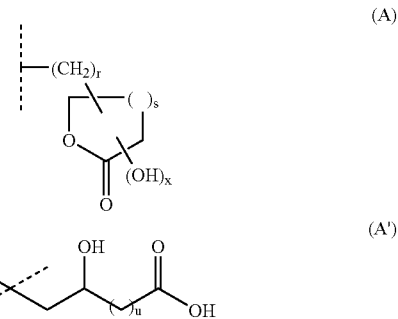

wherein x is 0 or 1, r is 0, 1, 2 or 3, s is 1 or 2 and u is 1 or 2; provided that the hydroxy group is not a substituent on the ring carbon adjacent to the ring oxygen;

$R^4$ is independently selected from hydrogen, halo, nitro, cyano, hydroxy, fluoromethyl, difluoromethyl, trifluoromethyl, trifluoromethoxy, carboxy, carbamoyl, $C_{1-4}$alkyl, $C_{2-4}$alkenyl, $C_{2-4}$alkynyl, $C_{1-4}$alkoxy and $C_{1-4}$alkanoyl;

B is phenyl or heterocyclyl;

$R^{14}$ is selected from hydrogen, halo, $C_{1-4}$alkyl (optionally substituted by 1 or 2 hydroxy groups), $C_{5-7}$cycloalkyl (optionally substituted with 1 or 2 hydroxy groups), $C_{1-4}$alkoxy, cyano, cyano($C_{1-4}$)alkyl, —$COR^3$, $(R^2)(R^3)$NCO—, and $(R^2)(R^3)NSO_2$—;

$R^2$ and $R^3$ are independently selected from $C_{5-7}$cycloalkyl (optionally substituted with 1 or 2 hydroxy groups), cyano($C_{1-4}$)alkyl, 5- and 6-membered cyclic acetals and mono- and di-methyl derivatives thereof, tetrahydrothiopyranyl, 1-oxotetrahydrothiopyranyl, 1,1-dioxotetrahydrothiopyranyl, fluoromethylcarbonyl, difluoromethylcarbonyl, trifluoromethylcarbonyl, $C_{1-4}$alkyl (optionally substituted with 1 or 2 $R^8$ groups), —$OR^8$ and $R^8$;

$R^8$ is independently selected from hydrogen, 2,2-dimethyl-1,3-dioxolan-4-yl, heterocyclyl (optionally substituted on ring carbon or ring nitrogen by 1 or 2 groups selected from hydrogen, nitro, halo, cyano, hydroxy and $C_{1-4}$alkyl), (heterocyclyl)$C_{1-4}$alkyl (wherein the heterocyclyl is optionally substituted on ring carbon or ring nitrogen by 1 or 2 groups selected from hydrogen, nitro, halo, cyano, hydroxy and $C_{1-4}$alkyl), aryl (optionally substituted by 1 or 2 groups selected from nitro, halo, cyano, hydroxy and $C_{1-4}$alkyl), $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS(O)$_c$($C_{1-4}$)alkyl (wherein c is 0, 1 or 2), —N(OH)CHO, —$CH_2CH(CO_2R^9)N(R^9R^{10})$, —$CH_2OR^9$, $(R^9)(R^{10})N$—, —$COOR^9$, —$CH_2COOR^9$, —$CH^2CONR^9R^{10}$ and —$(CH_2)_uCH(NR^9R^{10})CO_2R^9$ (wherein u is 1, 2 or 3);

$R^9$ and $R^{10}$ are independently selected from hydrogen, hydroxy, $C_{1-4}$alkyl (optionally substituted by 1 or 2 hydroxy groups), $C_{5-7}$cycloalkyl (optionally substituted by 1 or 2 hydroxy groups), $C_{2-4}$alkenyl, cyano($C_{1-4}$)alkyl, tetrahydrothiopyranyl, 1-oxotetrahydrothiopyranyl, 1,1-dioxotetrahydrothiopyranyl, 2,2-dimethyl-1,3-dioxolan-4-yl, aryl (optionally substituted by 1 or 2 substituents selected from hydrogen, nitro, halo, hydroxy and $C_{1-4}$alkyl) and $C_{1-4}$alkyl substituted by $R^{13}$; or $R^9$ and $R^{10}$ together with the nitrogen to which they are attached form a 4- to 6-membered ring where the ring is optionally substituted on carbon by 1 or 2 substituents selected from oxo, hydroxy, carboxy, halo, nitro, nitroso, cyano, isocyano, amino, N-$C_{1-4}$alkylamino, N,N-($C_{1-4}$alkyl)$_2$amino, carbonyl, $C_{1-4}$alkoxy, heterocyclyl, $C_{1-4}$alkanoyl, $C_{1-4}$alkylS(O)$_f$($C_{1-4}$)alkyl (wherein f is 0, 1 or 2), —N(OH)CHO, $(R^{11})(R^{12})$NCO—, $(R^{11})(R^{12})NSO_2$—, —$COCH^2OR^{11}$ and $(R^{11})(R^{12})N$—;

$R^{13}$ is selected from hydroxy, $C_{1-4}$alkoxy, heterocyclyl, $C_{1-4}$alkanoyl, $C_{1-4}$alkylS(O)$_d$ (wherein d is 0, 1 or 2), —N(OH)CHO, —$C(O)N(R^{11})(R^{12})$, $(R^{11})(R^{12})NSO_2$—, —$COCH^2OR^{11}$ and $(R^{11})(R^{12})N$—;

$R^{11}$ and $R^{12}$ are independently selected from hydrogen, $C_{1-4}$alkyl, $C_{1-4}$alkoxy, hydroxy$C_{1-4}$alkyl and $C_{1-4}$alkylS(O)$_e$ (wherein e is 0, 1 or 2);

or a pharmaceutically acceptable salt or pro-drug thereof.

According to another aspect of the present invention there is provided a compound of formula (1) wherein:

n is 0, 1 or 2;

m is 0, 1 or 2;

$R^1$ is independently selected from hydrogen, halo, nitro, cyano, hydroxy, amino, carboxy, carbamoyl, N-$C_{1-4}$alkylcarbamoyl, N,N-($C_{1-4}$alkyl)$_2$carbamoyl, sulphamoyl, N-$C_{1-4}$alkylsulphamoyl, N,N-($C_{1-4}$alkyl)$_2$sulphamoyl, sulfino, sulfo, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, hydroxy$C_{1-4}$alkyl, fluoromethyl, difluoromethyl, trifluoromethyl, trifluoromethoxy and $R^1$ is of the formula A or A':

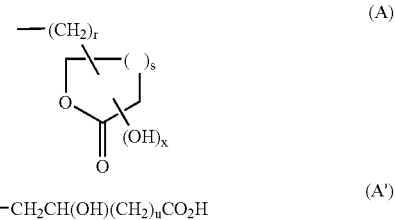

—$CH_2CH(OH)(CH_2)_uCO_2H$ (A')

wherein x is 0 or 1, r is 0, 1, 2 or 3 and s is 1 or 2; provided that the hydroxy group is not a substituent on the ring carbon adjacent to the ring oxygen;

$R^4$ is independently selected from hydrogen, halo, nitro, cyano, hydroxy, amino, carboxy, carbamoyl, N-$C_{1-4}$alkylcarbamoyl, NN-($C_{1-4}$alkyl)$_2$carbamoyl, sulphamoyl, N-$C_{1-4}$alkylsulphamoyl, N,N-($C_{1-4}$alkyl)$_2$sulphamoyl, sulfino, sulfo, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, hydroxy$C_{1-4}$alkyl, fluoromethyl, difluoromethyl, trifluoromethyl and trifluoromethoxy;

B is phenyl or heterocyclyl;

$R^{14}$ is selected from hydrogen, halo, $C_{1-4}$alkyl (optionally substituted by 1 or 2 hydroxy groups provided that when there are 2 hydroxy groups they are not substituents on the same carbon), $C_{5-7}$cycloalkyl (optionally substituted with 1 or 2 hydroxy groups provided that when there are 2 hydroxy groups they are not substituents on the same carbon), $C_{1-4}$alkoxy, cyano, cyano($C_{1-4}$)alkyl, —$COR^3$, $(R^2)(R^3)$NCO—, and $(R^2)(R^3)NSO_2$—;

{$R^2$ and $R^3$ are independently selected from $C_{1-4}$alkyl (substituted by 1 or 2 hydroxy groups provided that when there are 2 hydroxy groups they are not substituents on the same carbon), $C_{5-7}$cycloalkyl (optionally substituted with 1 or 2 hydroxy groups provided that when there are 2 hydroxy groups they are not substituents on the same carbon), cyano($C_{1-4}$)alkyl, 4-butanolidyl, 5-pentanolidyl, tetrahydrothiopyranyl, 1-oxotetrahydrothiopyranyl, 1,1-dioxotetrahydrothiopyranyl, fluoromethylcarbonyl, difluoromethylcarbonyl, trifluoromethylcarbonyl, $C_{1-4}$alkyl (substituted by $R^8$), —$OR^8$ and $R^8$;

[wherein $R^8$ is independently selected from hydrogen, 2,2-dimethyl-1,3-dioxolan-4-yl, heterocyclyl (optionally substituted on ring carbon or ring nitrogen by 1 or 2 groups selected from hydrogen, nitro, halo, cyano, hydroxy and $C_{1-4}$alkyl), (heterocyclyl)$C_{1-4}$alkyl (wherein the heterocyclyl is optionally substituted on ring carbon or ring nitrogen by 1 or 2 groups selected from hydrogen, nitro, halo, cyano, hydroxy and $C_{1-4}$alkyl), aryl (optionally substituted by 1 or 2 groups selected from nitro, halo, cyano, hydroxy and $C_{1-4}$alkyl), $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS(O)$_c$($C_{1-4}$)alkyl (wherein c is 0, 1 or 2), —N(OH)CHO, —$CH_2CH(CO_2R^9)N(R^9R^{10})$, —CH$_2$OR$^9$, (R$^9$)(R$^{10}$)N—, —COOR$^9$, —CH$_2$COOR$^9$, —CH$_2$CONR$^9$R$^{10}$ and —(CH$_2$)$_u$CH(NR$^9$R$^{10}$)CO$_2$R$^9$ (wherein u is 1, 2 or 3);

(wherein R$^9$ and R$^{10}$ are independently selected from hydrogen, hydroxy, C$_{1-4}$alkyl (optionally substituted by 1 or 2 hydroxy groups provided that when there are 2 hydroxy groups they are not substituents on the same carbon), C$_{5-7}$cycloalkyl (optionally substituted by 1 or 2 hydroxy groups provided that when there are 2 hydroxy groups they are not substituents on the same carbon), C$_{2-4}$alkenyl, cyano(C$_{1-4}$)alkyl, 4-butanolidyl, 5-pentanolidyl, tetrahydrothiopyranyl, 1-oxotetrahydrothiopyranyl, 1,1-dioxotetrahydrothiopyranyl, 2,2-dimethyl-1,3-dioxolan-4-yl, aryl (optionally substituted by 1 or 2 substituents selected from hydrogen, nitro, halo, hydroxy and C$_{1-4}$alkyl) and C$_{1-4}$alkyl substituted by R$^{13}$ {wherein R$^{13}$ is selected from hydroxy, C$_{1-4}$alkoxy, heterocyclyl, C$_{1-4}$alkanoyl, C$_{1-4}$alkylS(O)$_d$ (wherein d is 0, 1 or 2), —N(OH)CHO, (R$^{11}$)(R$^{12}$)NCO—, (R$^{11}$)(R$^{12}$)NSO$_2$—, —COCH$_2$OR$^{11}$, (R$^{11}$)(R$^{12}$)N—;

[wherein R$^{11}$ and R$^{12}$ are independently selected from hydrogen, C$_{1-4}$alkyl, C$_{1-4}$alkoxy, hydroxyC$_{1-4}$alkyl, C$_{1-4}$alkylS(O)$_e$ (wherein e is 0, 1 or 2)]}; and R$^9$ and R$^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N-C$_{1-4}$alkylamino, N,N-(C$_{1-4}$alkyl)$_2$amino, carbonyl, sulfo, C$_{1-4}$alkoxy, heterocyclyl, C$_{1-4}$alkanoyl, C$_{1-4}$alkylS(O)$_f$(C$_{1-4}$)alkyl (wherein f is 0, 1 or 2), —N(OH)CHO, (R$^{11}$)(R$^{12}$)NCO—, (R$^{11}$)(R$^{12}$)NSO$_2$—, —COCH$_2$OR$^{11}$, (R$^{11}$)(R$^{12}$)N—;

wherein R$^{11}$ and R$^{12}$ are as defined above)]};

or a pharmaceutically acceptable salt or in vivo hydrolysable ester thereof.

It is to be understood that, where optional substitution on alkyl or cycloalkyl groups in R$^2$, R$^3$, R$^9$, R$^{10}$, R$^{14}$ (as defined hereinbefore or hereinafter) allows two hydroxy substituents on the alkyl or cycloalkyl group, or one hydroxy substituent and a second substituent linked by a heteroatom (for example alkoxy), then these two substituents are not substituents on the same carbon atom of the alkyl or cycloalkyl group.

In another aspect, the invention relates to compounds of formula (1) as hereinabove defined or to a pharmaceutically acceptable salt.

In another aspect, the invention relates to compounds of formula (1) as hereinabove defined or to a pro-drug thereof. Suitable examples of pro-drugs of compounds of formula (1) are in-vivo hydrolysable esters of compounds of formula (1). Therefore in another aspect, the invention relates to compounds of formula (1) as hereinabove defined or to an in-vivo hydrolysable ester thereof.

It is to be understood that, insofar as certain of the compounds of formula (1) defined above may exist in optically active or racemic forms by virtue of one or more asymmetric carbon atoms, the invention includes in its definition any such optically active or racemic form which possesses glycogen phosphorylase inhibition activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

Within the present invention it is to be understood that a compound of the formula (1) or a salt thereof may exhibit the phenomenon of tautomerism and that the formulae drawings within this specification can represent only one of the possible tautomeric forms. It is to be understood that the invention encompasses any tautomeric form which has glycogen phosphorylase inhibition activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It is also to be understood that certain compounds of the formula (1) and salts thereof can exist in solvated as well as unsolvated forms such as, for example, hydrated forms. It is to be understood that the invention encompasses all such solvated forms which have glycogen phosphorylase inhibition activity.

It is also to be understood that certain compounds of the formula (1) may exhibit polymorphism, and that the invention encompasses all such forms which possess glycogen phosphorylase inhibition activity.

The present invention relates to the compounds of formula (1) as hereinbefore defined as well as to the salts thereof. Salts for use in pharmaceutical compositions will be pharmaceutically acceptable salts, but other salts may be useful in the production of the compounds of formula (1) and their pharmaceutically acceptable salts. Pharmaceutically acceptable salts of the invention may, for example, include acid addition salts of the compounds of formula (1) as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula (1) are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

The compounds of the invention may be administered in the form of a pro-drug which is broken down in the human or animal body to give a compound of the invention. A prodrug may be used to alter or improve the physical and/or pharmacokinetic profile of the parent compound and can be formed when the parent compound contains a suitable group or substituent which can be derivatised to form a prodrug. Examples of pro-drugs include in-vivo hydrolysable esters of a compound of the invention or a pharmaceutically-acceptable salt thereof.

Various forms of prodrugs are known in the art, for examples see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An in vivo hydrolysable ester of a compound of formula (1) containing carboxy or hydroxy group is, for example a pharmaceutically acceptable ester which is cleaved in the human or animal body to produce the parent acid or alcohol.

Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically-acceptable esters for hydroxy include inorganic esters such as phosphate esters (including phosphoramidic cyclic esters) and α-acyloxyalkyl ethers and related compounds which as a result of the in-vivo hydrolysis of the ester breakdown to give the parent hydroxy group/s. Examples of α-acyloxyalkyl ethers include acetoxymethoxy and 2,2-dimethylpropionyloxymethoxy. A selection of in-vivo hydrolysable ester forming groups for hydroxy include $C_{1-10}$alkanoyl, for example acetyl; benzoyl; phenylacetyl; substituted benzoyl and phenylacetyl, $C_{1-10}$alkoxycarbonyl (to give alkyl carbonate esters), for example ethoxycarbonyl; di-$(C_{1-4})$alkylcarbamoyl and N-(di-$(C_{1-4})$alkylaminoethyl)-N—$(C_{1-4})$alkylcarbamoyl (to give carbamates); di-$(C_{1-4})$alkylaminoacetyl and carboxyacetyl. Examples of ring substituents on phenylacetyl and benzoyl include aminomethyl, $(C_{1-4})$alkylaminomethyl and di-$((C_{1-4})$alkyl)aminomethyl, and morpholino or piperazino linked from a ring nitrogen atom via a methylene linking group to the 3- or 4-position of the benzoyl ring. Other interesting in-vivo hydrolysable esters include, for example, $R^A$C(O)O($C_{1-6}$)alkyl-CO—, wherein $R^A$ is for example, benzyloxy-$(C_{1-4})$alkyl, or phenyl). Suitable substituents on a phenyl group in such esters include, for example, 4-$(C_{1-4})$piperazino-$(C_{1-4})$alkyl, piperazino-$(C_{1-4})$alkyl and morpholino-$(C_1$-$C_4)$alkyl.

In this specification the generic term "alkyl" includes both straight-chain and branched-chain alkyl groups. However references to individual alkyl groups such as "propyl" are specific for the straight chain version only and references to individual branched-chain alkyl groups such as t-butyl are specific for the branched chain version only. For example, "$C_{1-4}$alkyl" includes methyl, ethyl, propyl, isopropyl and t-butyl. An analogous convention applies to other generic terms, for example "$C_{2-4}$alkenyl" includes vinyl, allyl and 1-propenyl and "$C_{2-4}$alkynyl" includes ethynyl, 1-propynyl and 2-propynyl.

The term "hydroxy$C_{1-4}$alkyl" includes hydroxymethyl, hydroxyethyl, hydroxypropyl, hydroxyisopropyl and hydroxybutyl. The term "hydroxyethyl" includes 1-hydroxyethyl and 2-hydroxyethyl. The term "hydroxypropyl" includes 1-hydroxypropyl, 2-hydroxypropyl and 3-hydroxypropyl and an analogous convention applies to terms such as hydroxybutyl. The term "dihydroxy$C_{1-4}$alkyl" includes dihydroxyethyl, dihydroxypropyl, dihydroxyisopropyl and dihydroxybutyl. The term "dihydroxypropyl" includes 1,2-dihydroxypropyl and 1,3-dihydroxypropyl. An analogous convention applies to terms such as dihydroxyisopropyl and dihydroxybutyl.

The term "halo" refers to fluoro, chloro, bromo and iodo. The term "dihalo$C_{1-4}$alkyl" includes difluoromethyl and dichloromethyl. The term "trihalo$C_{1-4}$alkyl" includes trifluoromethyl.

Examples of "5- and 6-membered cyclic acetals and mono- and di-methyl derivatives thereof" are:
1,3-dioxolan-4-yl, 2-methyl-1,3-dioxolan4-yl, 2,2-dimethyl-1,3-dioxolan4-yl; 2,2-dimethyl-1,3-dioxan-4-yl; 2,2-dimethyl-1,3-dioxan-5-yl; 1,3-dioxan-2-yl.

The term "sulfo" means $HOSO_2$—. The term "sulfino" means $HO_2S$—.

Examples of "$C_{1-4}$alkoxy" include methoxy, ethoxy, propoxy and isopropoxy. Examples of "$C_{1-4}$alkanoyl" include formyl, acetyl and propionyl. Examples of "$C_{1-4}$alkanoyloxy" are formyloxy, acetoxy and propionoxy. Examples of "N-($C_{1-4}$alkyl)amino" include methylamino and ethylamino. Examples of "N,N-($C_{1-4}$alkyl)$_2$amino" include N-N-(methyl)$_2$amino, N-N-(ethyl)$_2$amino and N-ethyl-N-methylamino. Examples of "N-($C_{1-4}$alkyl)carbamoyl" are methylcarbamoyl and ethylcarbamoyl. Examples of "N,N-($C_{1-4}$alkyl)$_2$carbamoyl" are N,N-(methyl)$_2$carbamoyl, N,N-(ethyl)$_2$carbamoyl and N-methyl-N-ethylcarbamoyl. Examples of "N-($C_{1-4}$alkyl)sulphamoyl" are N-(methyl)sulphamoyl and N-(ethyl)sulphamoyl. Examples of "N,N-($C_{1-4}$alkyl)$_2$sulphamoyl" are N,N-(methyl)$_2$sulphamoyl, N,N-(ethyl)$_2$sulphamoyl and N-(methyl)-N-(ethyl)sulphamoyl.

Examples of "cyano($C_{1-4}$)alkyl" are cyanomethyl, cyanoethyl and cyanopropyl. Examples of "$C_{5-7}$cycloalkyl" are cyclopentyl, cyclohexyl and cycloheptyl. Examples of "$C_{3-8}$cycloalkyl" and "$C_{3-7}$cycloalkyl" include "$C_{5-7}$cycloalkyl, cyclopropyl, cyclobutyl and cyclooctyl.

The term "amino$C_{1-4}$alkyl" includes aminomethyl, aminoethyl, aminopropyl, aminoisopropyl and aminobutyl. The term "aminoethyl" includes 1-aminoethyl and 2-aminoethyl. The term "aminopropyl" includes 1-aminopropyl, 2-aminopropyl and 3-aminopropyl and an analogous convention applies to terms such as aminoiosopropyl and aminobutyl.

Examples of "$C_{1-4}$alkylS(O)$_c$ (wherein c is 0 to 2)", "$C_{1-4}$alkylS(O)$_d$ (wherein d is 0 to 2)", "$C_{1-4}$alkylS(O)$_e$ (wherein e is 0 to 2)", and "$C_{1-4}$alkylS(O)$_f$ (wherein f is 0 to 2)" independently include methylthio, ethylthio, propylthio, methanesulphinyl, ethanesulphinyl, propanesulphinyl, mesyl, ethanesulphonyl, propanesulphonyl and isopropanesulphonyl.

Where optional substituents are chosen from "0, 1, 2 or 3" groups it is to be understood that this definition includes all substituents being chosen from one of the specified groups or the substituents being chosen from two or more of the specified groups. An analogous convention applies to substituents chose from "0, 1 or 2" groups and "1 or 2" groups.

"Heterocyclyl" is a saturated, partially saturated or unsaturated, optionally substituted monocyclic ring containing 5 to 7 atoms of which 1, 2, 3 or 4 ring atoms are chosen from nitrogen, sulphur or oxygen, which may, unless otherwise specified, be carbon or nitrogen linked, wherein a —$CH_2$— group can optionally be replaced by a —C(O)— and a ring sulphur atom may be optionally oxidised to form the S-oxide(s). Examples and suitable values of the term "heterocyclyl" are morpholino, morpholinyl, piperidino, piperidyl, pyridyl, pyranyl, pyrrolyl, imidazolyl, thiazolyl, thienyl, dioxolanyl, thiadiazolyl, piperazinyl, isothiazolidinyl, triazolyl, tetrazolyl, pyrrolidinyl, 2-oxazolidinonyl, 5-isoxazolonyl, thiomorpholino, pyrrolinyl, homopiperazinyl, 3,5-dioxapiperidinyl, 3-oxopyrazolin-5-yl, tetrahydropyranyl, tetrahydrothiopyranyl, 1-oxotetrahydrothiopyranyl, 1,1-dioxotetrahydrothiopyranyl, pyrimidyl, pyrazinyl, pyridazinyl, pyrazolyl, pyrazolinyl, isoxazolyl, 4-oxopyridyl, 2-oxopyrrolidyl, 4-oxothiazolidyl, furyl, thienyl, oxazolyl, and oxadiazolyl. Preferably "heterocyclyl" is morpholino, morpholinyl, piperidino, piperidyl, pyridyl, pyranyl, pyrrolyl, imidazolyl, thiazolyl, thienyl, thiadiazolyl, piperazinyl, isothiazolidinyl, 1,3,4-triazolyl, tetrazolyl, pyrrolidinyl, thiomorpholino, pyrrolinyl, homopiperazinyl, 3,5-dioxapiperidinyl, pyrimidyl, pyrazinyl, pyridazinyl, pyrazolyl, pyrazolinyl, isoxazolyl, 4-oxopyridyl, 2-oxopyrrolidyl, 4-oxothiazolidyl, furyl, thienyl, oxazolyl, 1,3,4-oxadiazolyl, and 1,2,4-oxadiazolyl. More preferably "heterocyclyl" is oxazolyl, 1,2,4-oxadiazolyl, pyridyl, furyl, thienyl, morpholine, pyrazinyl and piperazinyl.

Suitable optional substituents for "heterocyclyl" as a saturated or partially saturated ring are 1, 2 or 3 substituents independently selected from halo, cyano, hydroxy, $C_{1-4}$alkyl, $C_{1-4}$alkoxy and $C_{1-4}$alkylS(O)$_b$ (wherein b is 0, 1 or 2). Further suitable substituents for "heterocyclyl" as a saturated or partially saturated ring are 1, 2 or 3 substituents independently selected from fluoro, chloro, cyano, hydroxy, methyl, ethyl, methoxy, methylthio, methylsulfinyl and methylsulfonyl.

Suitable optional susbtituents for "heterocyclyl" as an unsaturated ring are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N-($C_{1-4}$ alkyl)amino and N,N-($C_{1-4}$alkyl)$_2$amino. Further suitable optional susbtituents for "heterocyclyl" as an unsaturated ring are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Examples of "(heterocyclyl)$C_{1-4}$alkyl" are morpholinomethyl, morpholinethyl, morpholinylmethyl, morpholinylethyl, piperidinomethyl, piperidinoethyl, piperidylmethyl, piperidylethyl, imidazolylmethyl, imidazolylethyl, oxazolylmethyl, oxazolylethyl, 1,3,4-oxadiazolylmethyl, 1,2,4-oxadiazolylmethyl, 1,2,4-oxadiazolylethyl, pyridylmethyl, pyridylethyl, furylmethyl, furylethyl, (thienyl)methyl, (thienyl)ethyl, pyrazinylmethyl, pyrazinylethyl, piperazinylmethyl and piperazinylethyl.

Examples of "aryl" are optionally substituted phenyl and naphthyl.

Examples of "aryl($C_{1-4}$)alkyl" are benzyl, 2-phenylethyl, naphthylmethyl and naphthylethyl.

Suitable optional substituents for "aryl" groups are 1, 2 or 3 substituents independently selected from halo, cyano, nitro, amino, hydroxy, $C_{1-4}$alkyl, $C_{1-4}$alkoxy, $C_{1-4}$alkylS(O)$_b$ (wherein b is 0, 1 or 2), N-($C_{1-4}$alkyl)amino and N,N-($C_{1-4}$ alkyl)$_2$amino. Further suitable optional susbtituents for "aryl" groups are 1, 2 or 3 substituents independently selected from fluoro, chloro, cyano, nitro, amino, methylamino, dimethylamino, hydroxy, methyl, ethyl, methoxy, methylthio, methylsulfinyl and methylsulfonyl.

Preferred values of B, $R^1$, $R^4$, $R^{14}$, m and n are as follows. Such values may be used where appropriate with any of the definitions, claims or embodiments defined hereinbefore or hereinafter.

In one embodiment of the invention are provided compounds of formula (1), in an alternative embodiment are provided pharmaceutically-acceptable salts of compounds of formula (1), in a further alternative embodiment are provided in-vivo hydrolysable esters of compounds of formula (1), and in a further alternative embodiment are provided pharmaceutically-acceptable salts of in-vivo hydrolysable esters of compounds of formula (1).

In one aspect of the invention n is 0 or 1.
Preferably n is 1.
In another aspect of the present invention $R^1$ is selected from hydrogen, halo, nitro, cyano, hydroxy, fluoromethyl, difluoromethyl, trifluoromethyl and groups of the formula A or A':

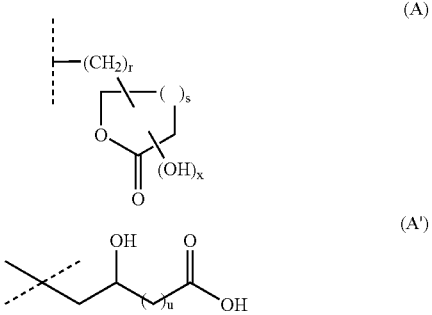

wherein x is 0 or 1, r is 0, 1, 2 or 3, s is 1 or 2 and u is 1 or 2; provided that the hydroxy group is not a substituent on the ring carbon adjacent to the ring oxygen;

Preferably $R^1$ is hydrogen or halo.
More preferably $R^1$ is hydrogen, chloro or fluoro.
In one aspect of the invention B is phenyl.
In another aspect of the invention B is heterocyclyl.
Preferably B is selected from phenyl, pyridyl, pyrimidinyl, pyrrolyl, thienyl, furyl, oxazole, isoxazole and oxadiazole.

In one aspect of the invention $R^{14}$ is selected from hydrogen, halo, $C_{1-4}$alkyl (optionally substituted by 1 or 2 hydroxy groups), $C_{5-7}$cycloalkyl (optionally substituted with 1 or 2 hydroxy groups), $C_{1-4}$alkoxy, cyano, cyano($C_{1-4}$) alkyl, —COR$^3$, ($R^2$)($R^3$)NCO—, and ($R^2$)($R^3$)NSO$_2$—;

wherein $R^2$ and $R^3$ are independently selected from $C_{1-4}$alkyl (substituted by 1 or 2 hydroxy groups), $C_{5-7}$cycloalkyl (optionally substituted with 1 or 2 hydroxy), cyano ($C_{1-4}$)alkyl, fluoromethylcarbonyl, difluoromethylcarbonyl, trifluoromethylcarbonyl, $C_{1-4}$alkyl (substituted by $R^8$), —OR$^8$ and $R^8$;

wherein $R^8$ is independently selected from hydrogen, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, 4-methylpiperazino, piperazinyl, $C_{1-4}$alkyl, $C_{2-4}$alkenyl, cyclo ($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS $(O)_c(C_{1-4})$alkyl (wherein c is 0, 1 or 2), —$CH_2CH(CO_2R^9)$N($R^9R^{10}$), —$CH_2OR^9$, $(R^9)(R^{10})N$—, —$COOR^9$ and —$CH_2COOR^9$, —$CH_2CONR^9R^{10}$, —$CH_2CH_2CH(NR^9R^{10})CO_2R^9$;

wherein $R^9$ and $R^{10}$ are independently selected from hydrogen, $C_{1-4}$alkyl (optionally substituted by 1 or 2 hydroxy groups), $C_{5-7}$cycloalkyl (optionally substituted by 1 or 2 hydroxy groups), $C_{2-4}$alkenyl, cyano($C_{1-4}$)alkyl, phenyl (optionally substituted by 1 or 2 groups selected from nitro, halo, hydroxy and cyano) and $C_{1-4}$alkyl substituted by $R^{13}$; or $R^9$ and $R^{10}$ together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N-$C_{1-4}$alkylamino, N,N-$(C_{1-4})_2$alkylamino, carbonyl, $C_{1-4}$alkoxy, heterocyclyl, $C_{1-4}$alkanoyl, and $C_{1-4}$alkylS$(O)_f$($C_{1-4}$)alkyl (wherein f is 0, 1 or 2);

wherein $R^{13}$ is selected from $C_{1-4}$alkoxy, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, $C_{1-4}$alkylS$(O)_d$($C_{1-4}$)alkyl (wherein d is 0, 1 or 2);

wherein $R^{11}$ is selected from hydrogen, $C_4$alkyl, $C_{1-4}$alkoxy, hydroxy$C_{1-4}$alkyl, $C_{1-4}$alkylS$(O)_e$ (wherein e is 0, 1 or 2).

In a further aspect of the invention $R^{14}$ is selected from hydrogen, —$COR^3$, $(R^2)(R^3)NCO$—, and $(R^2)(R^3)NSO_2$—;

wherein $R^2$ and $R^3$ are independently selected from $C_{1-4}$alkyl (substituted by 1 or 2 hydroxy groups), fluoromethylcarbonyl, difluoromethylcarbonyl, trifluoromethylcarbonyl, $C_{1-4}$alkyl (substituted by $R^8$), —$OR^8$ and $R^8$;

wherein $R^8$ is independently selected from hydrogen, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), phenyl (optionally substituted by 1 or 2 groups selected from nitro, halo, cyano and hydroxy), $C_{2-4}$alkenyl, cyclo($C_{3-8}$)alkyl, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), alkylS$(O)_c$($C_{1-4}$)alkyl (wherein c is 0, 1 or 2), —$CH_2CH(CO_2R^9)N(R^9R^{10})$, —$CH_2OR^9$, $(R^9)(R^{10})N$—, —$COOR^9$, —$CH_2COOR^9$, —$CH_2CONR^9R^{10}$, and —$CH_2CH_2CH(NR^9R^{10})CO_2R^9$;

wherein $R^9$ and $R^{10}$ are independently selected from hydrogen, $C_{1-4}$alkyl (optionally substituted by 1 or 2 hydroxy groups), $C_{2-4}$alkenyl, cyano($C_{1-4}$)alkyl and phenyl (optionally substituted by 1 or 2 groups selected from nitro, halo, hydroxy and cyano).

In another aspect of the invention $R^{14}$ is selected from hydrogen, —$COR^3$, $(R^2)(R^3)NCO$—, and $(R^2)(R^3)NSO_2$—;

wherein $R^2$ and $R^3$ are independently selected from $C_{1-4}$alkyl (substituted by $R^8$), —$OR^8$ and $R^8$;

wherein $R^8$ is independently selected from hydrogen, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), phenyl (optionally substituted by 1 or 2 groups selected from nitro, halo, cyano and hydroxy), $C_{2-4}$alkenyl, cyano($C_{1-4}$)alkyl, cyclo($C_{3-8}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl) and $C_{1-4}$alkylS$(O)_c$($C_{1-4}$)alkyl (wherein c is 0, 1 or 2).

In another aspect of the invention $R^{14}$ is selected from hydrogen, halo, cyano, $C_{1-4}$alkoxy, $C_{1-4}$alkyl (optionally substituted by 1 or 2 hydroxy groups) and cyano$C_{1-4}$alkyl.

In another aspect of the invention $R^{14}$ is selected from hydrogen, —$COR^3$, $(R^2)(R^3)NCO$—, and $(R^2)(R^3)NSO_2$—;

wherein $R^2$ is selected from hydrogen or $C_{1-4}$alkyl and $R^3$ is selected from hydrogen, methyl, hydroxyethyl, hydroxypropyl, 1,3-dihydroxyprop-2-yl, 3-hydroxy-2-hydroxymethylpropyl, 2,3-dihydroxypropyl, cyanomethyl, cyanoethyl, cyanopropyl, cyanomethylcarbonyl, cyanoethylcarbonyl, cyanopropylcarbonyl, carbamoyl, trifluoromethylcarbonyl, carboxymethanoyl, 4-amino-4-carboxybutanoyl, carboxyethyl, formyl, acetyl, propanoyl, methanesulfinyl, methanesulfonyl, morpholinomethylcarbonyl, phenylcarbonyl, furylcarbonyl, thienylcarbonyl, nitrofurylcarbonyl, pyrazinylcarbonyl, cyclopropylcarbonyl, morpholinocarbonyl, methylmercaptoethyl, N,N-(methyl)$_2$carbamoyl, 4-methylpiperazinocarbonyl, thienylsulfonyl, N-ethylcarbamoyl, N-allylcarbamoyl, N-dinitrophenylcarbamoyl, pyridinylcarbonyl, cyanophenylcarbonyl, hydroxyphenylcarbonyl, acryloyl, 2-amino-2-carboxyethylcarbonyl, 2-(tert-butoxycarbonyl)-2-(tert-butoxycarbonylamino)ethylcarbonyl, 2-(tert-butoxycarbonyl)ethylcarbonyl, aminobutanoyl, aminopropanoyl, aminoacetyl, N-methylaminoacetyl, 3-amino-3-carboxypropanoyl, chloroacetyl, hydroxyacetyl, N-methyl-N-hydroxyethylaminoacetyl, N-benzyl-N-hydroxyethylaminoacetyl, N-(2,3-dihydroxypropyl)-N-methylaminoacetyl, hydroxypiperidinoaminoacetyl, hydroxypyrrolidinylaminoacetyl and N,N-bis(hydroxyethyl)aminoacetyl.

In one aspect of the present invention m is 1 or 2.

In another aspect of the invention m is 1.

In one aspect of the present invention $R^4$ is selected from hydrogen, halo, cyano, hydroxy, fluoromethyl, difluoromethyl and trifluoromethyl.

In another aspect of the invention $R^4$ is hydrogen or halo.

Preferably $R^4$ is selected from hydrogen, chloro or bromo.

More preferably $R^4$ is chloro.

A preferred class of compound is of the formula (1) wherein;

n is 1 or 2;

$R^1$ is independently selected from hydrogen, halo, cyano, nitro, hydroxy, fluoromethyl, difluoromethyl, trifluoromethyl and groups of the formula A or A':

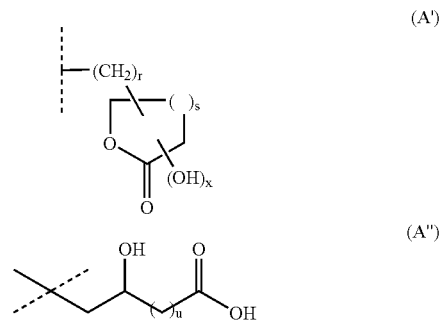

wherein x is 0 or 1, r is 0, 1, 2 or 3, s is 1 or 2 and u is 1 or 2; provided that the hydroxy group is not a substituent on the ring carbon adjacent to the ring oxygen;

B is heterocyclyl;

$R^{14}$ is selected from is selected from hydrogen, $C_{1-4}$alkyl (optionally substituted by 1 or 2 hydroxy groups), $C_{5-7}$cycloalkyl (optionally substituted with 1 or 2 hydroxy groups), cyano($C_{1-4}$)alkyl, -COR$^3$, $(R^2)(R^3)NCO$—, and $(R^2)(R^3)NSO_2$—;

$R^2$ and $R^3$ are independently selected from $C_{1-4}$alkyl (substituted by 1 or 2 hydroxy groups), $C_{5-7}$cycloalkyl (optionally substituted with 1 or 2 hydroxy groups), cyano($C_{1-4}$)alkyl, fluoromethylcarbonyl, difluoromethylcarbonyl, trifluoromethylcarbonyl, $C_{1-4}$alkyl (substituted by $R^8$), —OR$^8$ and $R^8$;

$R^8$ is independently selected from hydrogen, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, morpholino, pyridyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS(O)$_c$($C_{1-4}$)alkyl (wherein c is 0, 1 or 2), —CH$_2$CH(CO$_2$R$^9$)N(R$^9$R$^{10}$), —CH$_2$OR$^9$, $(R^9)(R^{10})N$—, —COOR$^9$, —CH$_2$COOR$^9$, —CH$_2$CONR$^9$R$^{10}$, and —CH$_2$CH$_2$CH(NR$^9$R$^{10}$)CO$_2$R$^9$;

$R^9$ and $R^{10}$ are independently selected from hydrogen, $C_{1-4}$alkyl (optionally substituted by 1 or 2 hydroxy groups), $C_{5-7}$cycloalkyl (optionally substituted by 1 or 2 hydroxy groups), $C_{2-4}$alkenyl, cyano($C_{1-4}$)alkyl, phenyl (optionally substituted by 1 or 2 groups selected from nitro, halo, hydroxy and cyano) and $C_{1-4}$alkyl substituted by $R^{13}$; or $R^9$ and $R^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N-C$_{1-4}$alkylamino, N,N-(C$_{1-4}$)$_2$alkylamino, carbonyl, C$_{1-4}$alkoxy, heterocyclyl, C$_{1-4}$alkanoyl, and C$_{1-4}$alkylS(O)$_f$(C$_{1-4}$)alkyl (wherein f is 0, 1 or 2);

$R^{13}$ is selected from $C_{1-4}$alkoxy, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, $C_{1-4}$alkylS(O)$_d$($C_{1-4}$)alkyl (wherein d is 0, 1 or 2);

m is 1 or 2;

$R^4$ is hydrogen or halo;

or a pharmaceutically acceptable salt or in-vivo hydrolysable ester thereof.

Another preferred class of compound is of the formula (1) wherein:

n is 1 or 2;

$R^1$ is independently selected from hydrogen, halo, nitro, hydroxy, $C_{1-4}$alkyl and groups of the formula A or A':

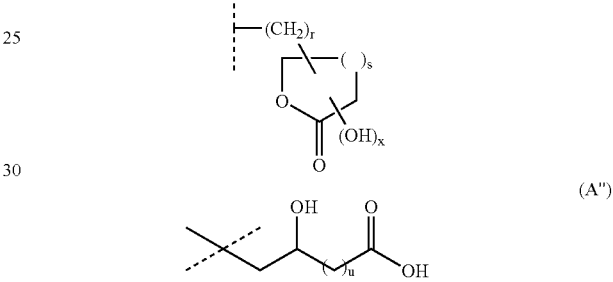

wherein x is 0 or 1, r is 0, 1, 2 or 3, s is 1 or 2 and u is 1 or 2; provided that the hydroxy group is not a substituent on the ring carbon adjacent to the ring oxygen;

B is heterocyclyl;

$R^{14}$ is selected from is selected from hydrogen, $C_{1-4}$alkyl, cyano($C_{1-4}$)alkyl, —COR$^3$, $(R^2)(R^3)NCO$—, and $(R^2)(R^3)NSO_2$—;

$R^2$ and $R^3$ are independently selected from $C_{1-4}$alkyl (substituted by 1 or 2 hydroxy groups), cyano($C_{1-4}$)alkyl, trifluoromethylcarbonyl, $C_{1-4}$alkyl (substituted by $R^8$), —OR$^8$ and $R^8$;

$R^8$ is independently selected from hydrogen, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, 4-methylpiperazino, $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy(Cl 4)alkyl, aryl and aryl($C_{1-4}$)alkyl), $C_{1-4}$alkylS(O)$_c$($C_{1-4}$)alkyl (wherein c is 0, 1 or 2), —CH$_2$CH(CO$_2$R$^9$)N(R$^9$R$^{10}$), —CH$_2$OR$^9$, $(R^9)(R^{10})N$—, —COOR$^9$, —CH$_2$COOR$^9$, —CH$_2$CONR$^9$R$^{10}$, and —CH$_2$CH$_2$CH(NR$^9$R$^{10}$)CO$_2$R$^9$;

$R^9$ and $R^{10}$ are independently selected from hydrogen, $C_{1-4}$alkyl (optionally substituted by 1 or 2 hydroxy groups), $C_{5-7}$cycloalkyl (optionally substituted by 1 or 2 hydroxy groups), $C_{2-4}$alkenyl, cyano($C_{1-4}$)alkyl and phenyl (optionally substituted by 1 or 2 groups selected from nitro, halo, hydroxy and cyano); or $R^9$ and $R^{10}$ can together with the nitrogen to which they are attached form 4- to 6-membered ring where the ring is optionally substituted on carbon by 1 or 2 substituents selected from oxo, hydroxy, carboxy, halo, nitro, nitroso, cyano, isocyano, amino, N-$C_{1-4}$alkylamino, N,N-($C_{1-4}$)$_2$alkylamino, carbonyl, $C_{1-4}$alkoxy, heterocyclyl, $C_{1-4}$alkanoyl, and $C_{1-4}$alkylS(O)$_f$($C_{1-4}$)alkyl (wherein f is 0, 1 or 2);

m is 1 or 2;

$R^4$ is hydrogen or halo;

or a pharmaceutically acceptable salt or in-vivo hydrolysable ester thereof.

Another preferred class of compound is of the formula (1) wherein:

n is 1 or 2;

$R^1$ is independently selected from hydrogen, halo, nitro, hydroxy, $C_{1-4}$alkyl and groups of the formula A or A':

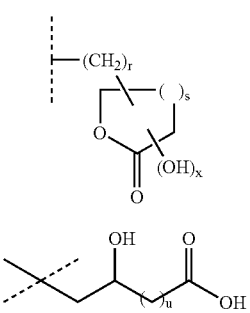

wherein x is 0 or 1, r is 0, 1, 2 or 3, s is 1 or 2 and u is 1 or 2; provided that the hydroxy group is not a substituent on the ring carbon adjacent to the ring oxygen;

B is heterocyclyl;

$R^{14}$ is selected from is selected from $C_{1-4}$alkyl, cyano($C_{1-4}$)alkyl, —COR$^3$, ($R^2$)($R^3$)NCO—, and ($R^2$)($R^3$)NSO$_2$—;

$R^2$ and $R^3$ are independently selected from $C_{1-4}$alkyl, $C_{1-4}$alkyl (substituted by $R^8$), —OR$^8$ and $R^8$;

$R^8$ is independently selected from hydrogen, furyl (optionally substituted on carbon by 1 or 2 nitro groups), thienyl (optionally substituted on carbon by 1 or 2 nitro groups), morpholino, furyl($C_{1-4}$)alkyl (wherein furyl is optionally substituted on carbon by 1 or 2 nitro groups), thienyl($C_{1-4}$)alkyl (wherein thienyl is optionally substituted on carbon by 1 or 2 nitro groups), 1,2,4-oxadiazolyl, tetrazolyl, imidazolyl, pyrrolidinyl, piperidyl, tetrahydrofuryl, tetrahydropyranyl, tetrahydrothiopyranyl, tetrahydrothienyl, phenyl (optionally substituted by 1 or 2 groups selected from nitro, halo, cyano, hydroxy and $C_{1-4}$alkyl), pyrazinyl, piperazinyl, $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS(O)$_c$($C_{1-4}$)alkyl (wherein c is 0, 1 or 2), —CH$_2$CH(CO$_2$R$^9$)N(R$^9$R$^{10}$), —CH$_2$OR$^9$, ($R^9$)($R^{10}$)N—, —COOR$^9$, —CH$_2$COOR$^9$, —CH$_2$CONR$^9$R$^{10}$, and —CH$_2$CH$_2$CH(NR$^9$R$^{10}$)CO$_2$R$^9$;

$R^9$ and $R^{10}$ are independently $C_{1-4}$alkenyl or phenyl (optionally substituted by nitro, halo or cyano);

m is 1;

$R^4$ is chloro;

or a pharmaceutically acceptable salt or in-vivo hydrolysable ester thereof.

Another preferred class of compound is of the formula (1) wherein:

n is 1 or 2;

$R^1$ is independently selected from hydrogen, halo, nitro, hydroxy, $C_{1-4}$alkyl and groups of the formula A or A':

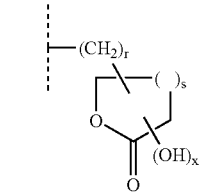

wherein x is 0 or 1, r is 0, 1, 2 or 3, s is 1 or 2 and u is 1 or 2; provided that the hydroxy group is not a substituent on the ring carbon adjacent to the ring oxygen;

B is heterocyclyl;

$R^{14}$ is selected from hydrogen, halo, cyano, $C_{1-4}$alkoxy, $C_{1-4}$alkyl (optionally substituted by 1 or 2 hydroxy groups provided that when there are 2 hydroxy groups they are not substituents on the same carbon) and cyano$C_{1-4}$alkyl;

m is 1;

$R^4$ is chloro;

or a pharmaceutically acceptable salt or in-vivo hydrolysable ester thereof.

Another preferred class of compound is of the formula (1) wherein:

n is 1 or 2;

$R^1$ is independently selected from hydrogen, halo, nitro, hydroxy, $C_{1-4}$alkyl and $R^1$ is of the formula A or A':

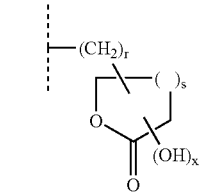

wherein x is 0 or 1, r is 0, 1, 2 or 3, s is 1 or 2 and u is 1 or 2; provided that the hydroxy group is not a substituent on the ring carbon adjacent to the ring oxygen;

B is phenyl;

$R^{14}$ is selected from is selected from $C_{1-4}$alkyl, cyano$(C_{1-4})$alkyl, —$COR^3$, $(R^2)(R^3)NCO$—, and $(R^2)(R^3)NSO_2$—;

$R^2$ and $R^3$ are independently selected from $C_{1-4}$alkyl, $C_{1-4}$alkyl (substituted by $R^8$), —$OR^8$ and $R^8$;

$R^8$ is independently selected from hydrogen, heterocyclyl (optionally substituted on carbon or nitrogen by 1 or 2 groups selected from nitro, halo, hydroxy, cyano and $C_{1-4}$alkyl), (heterocyclyl)($C_{1-4}$)alkyl (optionally substituted on carbon or nitrogen by 1 or 2 groups selected from nitro, halo, hydroxy, cyano and $C_{1-4}$alkyl), aryl (optionally substituted by 1 or 2 groups selected from nitro, halo, cyano, hydroxy and $C_{1-4}$alkyl), $C_{1-4}$alkyl, $C_{2-4}$alkenyl, cyclo($C_{3-8}$)alkyl, $C_{1-4}$alkoxy, cyano($C_{1-4}$)alkyl, amino($C_{1-4}$)alkyl (optionally substituted on nitrogen by 1 or 2 groups selected from hydrogen, $C_{1-4}$alkyl, hydroxy, hydroxy($C_{1-4}$)alkyl, dihydroxy($C_{1-4}$)alkyl, aryl and aryl($C_{1-4}$)alkyl), $C_{1-4}$alkylS$(O)_c(C_{1-4})$alkyl (wherein c is 0, 1 or 2), —$(CH_2)_uCH(CO_2R^9)N(R^9R^{10})$ (wherein u is 0, 1 or 2), —$CH_2OR^9$, $(R^9)(R^{10})N$—, —$COOR^9$ and —$CH_2COOR^9$, —$CH_2CONR^9R^{10}$, —$CH_2CH_2CH(NR^9R^{10})CO_2R^9$;

$R^9$ and $R^{10}$ are independently selected from hydrogen, $C_{1-4}$alkyl (optionally substituted by 1 or 2 hydroxy groups), $C_{5-7}$cycloalkyl (optionally substituted by 1 or 2 hydroxy groups), $C_{2-4}$alkenyl, cyano($C_{1-4}$)alkyl, and phenyl (optionally substituted by 1 or 2 groups selected from nitro, halo, hydroxy and cyano);

m is 1;

$R^4$ is chloro; or a pharmaceutically acceptable salt or in-vivo hydrolysable ester thereof.

In another aspect of the invention, preferred compounds of the invention are any one of:

methyl (S)-5-{1-[(5-chloro-1H-indol-2-ylcarbonyl)amino]-2-phenylethyl}oxazole-4-carboxylate;

or a pharmaceutically acceptable salt or an in vivo hydrolysable ester thereof.

Another aspect of the present invention provides a process for preparing a compound of formula (1) or a pharmaceutically acceptable salt or an in vivo hydrolysable ester thereof which process (wherein B, $R^1$, $R^4$, $R^{14}$ m and n are, unless otherwise specified, as defined in formula (1)) comprises of:

a) reacting an acid of the formula (2):

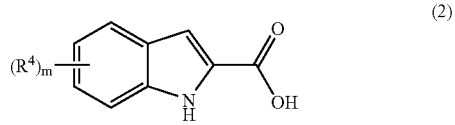

(2)

or an activated derivative thereof, with an amine of formula (3):

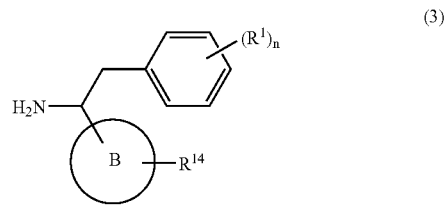

(3)

and thereafter if necessary:

i) converting a compound of the formula (1) into another compound of the formula (1);

ii) removing any protecting groups;

iii) forming a pharmaceutically acceptable salt or in vivo hydrolysable ester.

Specific reaction conditions for the above reaction are as follows.

Process a) Acids of formula (2) and amines of formula (3) may be coupled together in the presence of a suitable coupling reagent. Standard peptide coupling reagents known in the art can be employed as suitable coupling reagents, or for example carbonyldiimidazole, 1-ethyl-3-(3-dimethylaminopropyl)carbodi-imide hydrochloride and dicyclohexyl-carbodiimide, optionally in the presence of a catalyst such as 1-hydroxybenzotriazole, dimethylaminopyridine or 4-pyrrolidinopyridine, optionally in the presence of a base for example triethylamine, di-isopropylethylamine, pyridine, or 2,6-dialkylpyridines such as 2,6-lutidine or 2,6-di-tert-butylpyridine. Suitable solvents include dimethylacetamide, dichloromethane, benzene, tetrahydrofuran and dimethylformamide. The coupling reaction may conveniently be performed at a temperature in the range of −40 to 40° C.

Suitable activated acid derivatives include acid halides, for example acid chlorides, and active esters, for example pentafluorophenyl esters. The reaction of these types of compounds with amines is well known in the art, for example they may be reacted in the presence of a base, such as those described above, and in a suitable solvent, such as those described above. The reaction may conveniently be performed at a temperature in the range of −40 to 40° C.

The acids of formula (2) are commercially available or they are known compounds or they are prepared by processes known in the art.

Processes for the preparation of compounds of formula (3) often involve heterocyclic ring formation. Compounds of formula (3) may therefore be prepared by processes known in the art and in particular with reference to Alan R. Katritzky, Comprehensive Heterocyclic Chemistry, Pergamon Press. Processes for the preparation of compounds of formua (3) may also be found in Tett. Letts., Vol 23, no 2, p 235.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogen group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl.

It will also be appreciated that in some of the reactions mentioned herein it may be necessary/desirable to protect any sensitive groups in the compounds. The instances where protection is necessary or desirable and suitable methods for protection are known to those skilled in the art. Conventional protecting groups may be used in accordance with standard practice (for illustration see T. W. Green, Protective Groups in Organic Synthesis, John Wiley and Sons, 1991). Thus, if reactants include groups such as amino, carboxy or hydroxy it may be desirable to protect the group in some of the reactions mentioned herein.

A suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed for example, by hydrolysis with a suitable base such as an alkali metal hydroxide, for example lithium or sodium hydroxide. Alternatively an acyl group such as a t-butoxycarbonyl group may beremoved, for example, by treatment with a suitable acid as hydrochloric, sulphuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium or sodium hydroxide. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

The protecting groups may be removed at any convenient stage in the synthesis using conventional techniques well known in the chemical art.

Certain intermediates in the preparation of a compound of the formula (1) are novel and form another aspect of the invention.

As stated hereinbefore the compounds defined in the present invention possesses glycogen phosphorylase inhibitory activity. This property may be assessed, for example, using the procedure set out below.

Assay

The activity of the compounds is determined by measuring the inhibitory effect of the compounds in the direction of glycogen synthesis, the conversion of glucose-1-phosphate into glycogen with the release of inorganic phosphate, as described in EP 0 846 464 A2. The reactions were in 96 well microplate format in a volume of 100 µl. The change in optical density due to inorganic phosphate formation was measured at 620 nM in a Labsystems iEMS Reader MF by the general method of (Nordlie R. C and Arion W. J, Methods of Enzymology, 1966, 619–625). The reaction is in 50 mM HEPES (N-(2-Hydroxyethyl)piperazine-N'-(2-ethanesulfonic acid);4-(2-Hydroxyethyl)piperazine-1-ethanesulfonic acid), 2.5 mM $MgCl_2$, 2.25 mM ethylene glycol-bis(b-aminoethyl ether) N,N,N',N'-tetraacetic acid, 100 mM KCl, 2 mM D-(+)-glucose pH7.2, containing 0.5 mM dithiothreitol, the assay buffer solution, with 0.1 mg type III glycogen, 0.15 ug glycogen phosphorylase a (GPa) from rabbit muscle and 0.5 mM glucose-1-phosphate. GPa is pre-incubated in the assay buffer solution with the type III glycogen at 2.5 mg ml$^{-1}$ for 30 minutes. 40 µl of the enzyme solution is added to 25 µl assay buffer solution and the reaction started with the addition of 25 µl 2 mM glucose-1-phosphate. Compounds to be tested are prepared in 10 µl 10% DMSO in assay buffer solution, with final concentration of 1% DMSO in the assay. The non-inhibited activity of GPa is measured in the presence of 10 µl 10% DMSO in assay buffer solution and maximum inhibition measured in the presence of 30 µM CP320626 (Hoover et al (1998) J Med Chem 41, 2934–8; Martin et al (1998) PNAS 95, 1776–81). The reaction is stopped after 30 min with the addition of 50 µl acidic ammonium molybdate solution, 12 ug ml$^{-1}$ in 3.48% $H_2SO_4$ with 1% sodium lauryl sulphate and 10 ug ml$^{-1}$ ascorbic acid. After 30 minutes at room temperature the absorbency at 620 nm is measured.

The assay is performed at a test concentration of inhibitor of 10 µM or 100 µM. Compounds demonstrating significant inhibition at one or both of these concentrations may be further evaluated using a range of test concentrations of inhibitor to determine an $IC_{50}$, a concentration predicted to inhibit the enzyme reaction by 50%.

Activity is calculated as follows:

% inhibition=(1−(compound OD620−fully inhibited OD620)/(non-inhibited rate OD620−fully inhibited OD620))*100.

OD620=optical density at 620 nM.

Typical $IC_{50}$ values for compounds of the invention when tested in the above assay are in the range 100 µM to 1 nM.

The activity of the compounds is alternatively determined by measuring the inhibitory effect of the compounds on glycogen degradation, the production of glucose-1-phosphate from glycogen is monitored by the multienzyme coupled assay, as described in EP 0 846 464 A2, general method of Pesce et al (Pesce, M A, Bodourian, S H, Harris, R C, and Nicholson, J F (1977) Clinical Chemistry 23, 1171–1717). The reactions were in 384 well microplate format in a volume of 50 µl. The change in fluorescence due to the conversion of the co-factor NAD to NADH is measured at 340 nM excitation, 465 nm emission in a Tecan Ultra Multifunctional Microplate Reader. The reaction is in 50 OmM HEPES, 3.5 mM $KH_2PO_4$, 2.5 mM $MgCl_2$, 2.5 mM ethylene glycol-bis(b-aminoethyl ether) N,N,N',N'-tetraacetic acid, 100 mM KCl, 8 mM D-(+)-glucose pH7.2, containing 0.5 mM dithiothreitol, the assay buffer solution. Human recombinant liver glycogen phosphorylase a (hrl GPa) 20 nM is pre-incubated in assay buffer solution with 6.25 mM NAD, 1.25 mg type III glycogen at 1.25 mg ml$^{-1}$ the reagent buffer, for 30 minutes. The coupling enzymes, phosphoglucomutase and glucose-6-phosphate dehydrogenase (Sigma) are prepared in reagent buffer, final concentration 0.25 Units per well. 20 μl of the hrl GPa solution is added to 10 μl compound solution and the reaction started with the addition of 20 ul coupling enzyme solution. Compounds to be tested are prepared in 10 μl 5% DMSO in assay buffer solution, with final concentration of 1% DMSO in the assay. The non-inhibited activity of GPa is measured in the presence of 10 μl 5% DMSO in assay buffer solution and maximum inhibition measured in the presence of 5 mgs ml$^{-1}$ N-ethylmaleimide. After 6 hours at 30° C. Relative Fluoresence Units (RFUs) are measured at 340 nM excitation, 465 nm emission.

The assay is performed at a test concentration of inhibitor of 10 μM or 100 μM. Compounds demonstrating significant inhibition at one or both of these concentrations may be further evaluated using a range of test concentrations of inhibitor to determine an IC$_{50}$, a concentration predicted to inhibit the enzyme reaction by 50%.

Activity is calculated as follows:

% inhibition=(1−(compound RFUs−fully inhibited RFUs)/(non-inhibited rate RFUs−fully inhibited RFUs))*100.

Typical IC$_{50}$ values for compounds of the invention when tested in the above assay are in the range 100 μM to 1 nM. For example, Example 1 gave an IC$_{50}$ value of 2.4 μM.

The inhibitory activity of compounds was further tested in rat primary hepatocytes.

Rat hepatocytes were isolated by the collagenase perfusion technique, general method of Seglen (P. O. Seglen, Methods Cell Biology (1976) 13 29–83). Cells were cultured on Nunclon six well culture plates in DMEM with high level of glucose containing 10% foetal calf serum, NEAA, Glutamine, penicillin /streptomycin ((100 units/100 ug)/ml) for 4 to 6 hours. The hepatocytes were then cultured in the DMEM solution without foetal calf serum and with 10 nM insulin and 10 nM dexamethasone. Experiments were initiated after 18–20 hours culture by washing the cells and adding Krebs-Henseleit bicarbonate buffer containing 2.5mM CaCl$_2$ and 1% gelatin. The test compound was added and 5 minutes later the cells were challenged with 25 nM glucagon. The Krebs-Henseleit solution was removed after 60 min incubation at 37° C., 95% O$_2$/5% CO$_2$ and the glucose concentration of the Krebs-Henseleit solution measured.

According to a further aspect of the invention there is provided a pharmaceutical composition which comprises a compound of the formula (1), or a pharmaceutically acceptable salt or in vivo hydrolysable ester thereof, as defined hereinbefore in association with a pharmaceutically-acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above.

Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The compound of formula (1) will normally be administered to a warm-blooded animal at a unit dose within the range 5–5000 mg per square meter body area of the animal, i.e. approximately 0.1–100 mg/kg, and this normally provides a therapeutically-effective dose. A unit dose form such as a tablet or capsule will usually contain, for example, 1–250 mg of active ingredient. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The inhibition of glycogen phosphorylase activity described herein may be applied as a sole therapy or may involve, in addition to the subject of the present invention, one or more other substances and/or treatments. Such conjoint treatment may be achieved by way of the simultaneous, sequential or separate administration of the individual components of the treatment. Simultaneous treatment may be in a single tablet or in separate tablets. For example in the treatment of diabetes mellitus chemotherapy may include the following main categories of treatment:

1) Insulin and insulin analogues;
2) Insulin secretagogues including sulphonylureas (for example glibenclamide, glipizide) and prandial glucose regulators (for example repaglinide, nateglinide);
3) Insulin sensitising agents including PPARg agonists (for example pioglitazone and rosiglitazone);
4) Agents that suppress hepatic glucose output (for example metformin).
5) Agents designed to reduce the absorption of glucose from the intestine (for example acarbose);
6) Agents designed to treat the complications of prolonged hyperglycaemia;
7) Anti-obesity agents (for example sibutramine and orlistat);
8) Anti- dyslipidaemia agents such as, HMG-CoA reductase inhibitors (statins, eg pravastatin); PPAR$\alpha$ agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations);
9) Antihypertensive agents such as, $\beta$ blockers (eg atenolol, inderal); ACE inhibitors (eg lisinopril); Calcium antagonists (eg. nifedipine); Angiotensin receptor antagonists (eg candesartan), oc antagonists and diuretic agents (eg. furosemide, benzthiazide);
10) Haemostasis modulators such as, antithrombotics, activators of fibrinolysis and antiplatelet agents; thrombin antagonists; factor Xa inhibitors; factor VIIa inhibitors); antiplatelet agents (eg. aspirin, clopidogrel); anticoagulants (heparin and Low molecular weight analogues, hirudin) and warfarin; and
11) Anti-inflammatory agents, such as non-steroidal anti-inflammatory drugs (eg. aspirin) and steroidal anti-inflammatory agents (eg. cortisone).

According to a further aspect of the present invention there is provided a compound of the formula (1), or a pharmaceutically acceptable salt or in vivo hydrolysable ester thereof, as defined hereinbefore, for use in a method of treatment of a warm-blooded animal such as man by therapy.

According to an additional aspect of the invention there is provided a compound of the formula (1), or a pharmaceutically acceptable salt or in vivo hydrolysable ester thereof, as defined hereinbefore, for use as a medicament.

According to an additional aspect of the invention there is provided a compound of the formula (1), or a pharmaceutically acceptable salt or in vivo hydrolysable ester thereof, as defined hereinbefore, for use as a medicament in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes, insulin resistance, syndrome X, hyperinsulinaemia, hyperglucagonaemia, cardiac ischaemia or obesity in a warm-blooded animal such as man.

According to this another aspect of the invention there is provided the use of a compound of the formula (1), or a pharmaceutically acceptable salt or in vivo hydrolysable ester thereof, as defined hereinbefore in the manufacture of a medicament for use in the treatment of type 2 diabetes in a warm-blooded animal such as man.

According to a further feature of this aspect of the invention there is provided a method of producing a glycogen phosphorylase inhibitory effect in a warm-blooded animal, such as man, in need of such treatment which comprises administering to said animal an effective amount of a compound of formula (1).

According to this further feature of this aspect of the invention there is provided a method of treating type 2 diabetes, insulin resistance, syndrome X, hyperinsulinaemia, hyperglucagonaemia, cardiac ischaemia or obesity in a warm-blooded animal, such as man, in need of such treatment which comprises administering to said animal an effective amount of a compound of formula (1).

According to this further feature of this aspect of the invention there is provided a method of treating type 2 diabetes in a warm-blooded animal, such as man, in need of such treatment which comprises administering to said animal an effective amount of a compound of formula (1).

As stated above the size of the dose required for the therapeutic or prophylactic treatment of a particular cell-proliferation disease will necessarily be varied depending on the host treated, the route of administration and the severity of the illness being treated. A unit dose in the range, for example, 1–100 mg/kg, preferably 1–50 mg/kg is envisaged.

In addition to their use in therapeutic medicine, the compounds of formula (1) and their pharmaceutically acceptable salts are also useful as pharmacological tools in the development and standardisation of in vitro and in vivo test systems for the evaluation of the effects of inhibitors of cell cycle activity in laboratory animals such as cats, dogs, rabbits, monkeys, rats and mice, as part of the search for new therapeutic agents.

In the above other pharmaceutical composition, process, method, use and medicament manufacture features, the alternative and preferred embodiments of the compounds of the invention described herein also apply.

EXAMPLES

The invention will now be illustrated by the following non-limiting examples in which, unless stated otherwise:
(i) temperatures are given in degrees Celsius (° C.); operations were carried out at room or ambient temperature, that is, at a temperature in the range of 18–25° C. and under an atmosphere of an inert gas such as argon;
(ii) organic solutions were dried over anhydrous magnesium sulphate; evaporation of solvent was carried out using a rotary evaporator under reduced pressure (600–4000 Pascals; 4.5–30 mmHg) with a bath temperature of up to 60° C.;
(iii) in general, the course of reactions was followed by TLC and reaction times are given for illustration only;
(iv) yields are given for illustration only and are not necessarily those which can be obtained by diligent process development; preparations were repeated if more material was required;
(v) where given, NMR data is in the form of delta values for major diagnostic protons, given in parts per million (ppm) relative to tetramethylsilane (TMS) as an internal standard, determined at 300 MHz using perdeuterio dimethyl sulphoxide (DMSO-$d_6$) as solvent unless otherwise indicated, other solvents (where indicated in the text) include deuterated chloroform $CDCl_3$;
(vi) chemical symbols have their usual meanings; SI units and symbols are used;
(vii) solvent ratios are given in volume : volume (v/v) terms;
(viii) The following abbreviations are used:

| | |
|---|---|
| EtOAc | ethyl acetate; |
| DCM | dichloromethane; |
| HOBT | 1-hydroxybenzotriazole; |
| DIPEA | di-isopropylethylamine; |
| EDAC | 1-ethyl-3-(3-dimethylaminopropyl)carbodi-imide hydrochloride; |

Example 1

Methyl (S)-5-{1-[(5-chloro-1H-indol-2-ylcarbonyl)amino]-2-phenylethyl}oxazole-4-carboxylate

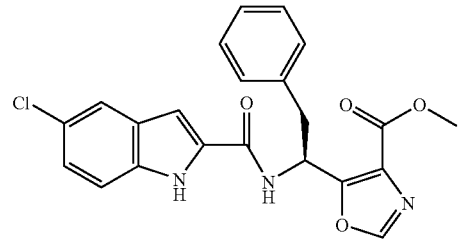

2-Carboxy-5-chloro-indole (146 mg, 0.75 mmol) was dissolved in DCM (5 ml) containing HOBT (126 mg, 0.93 mmol), DIPEA (290 mg, 2.25 mmol) and methyl (s)-5-(1-amino-2-phenylethyl)oxazole-4-carboxylate trifluoroacetate (Method 1; 360 mg, 0.75 mmol). EDAC (178 mg, 0.93 mmol) was added and the mixture stirred at ambient temperature for 4 hours. The reaction mixture was diluted with ethyl acetate (30 ml), washed with dilute citric acid, water and brine, dried over magnesium sulphate and concentrated. The crude material was purified by trituration with diethyl ether to give the title compound as a white solid. (227 mg, 65%)

NMR 3.1–3.2 (1H, m); 3.25–3.3 (1H, m); 3.8 (3H, s); 5.9–6.0 (1H, m); 7.1–7.3 (7H, m); 7.4 (1H, d); 7.75 (1H, d); 8.46 (1H, s); 9.1 (1H, d); 11.68 (1H, bs)

Method 1

Methyl (S)-5-(1-amino-2-phenylethyl)oxazole-4-carboxylate trifluoroacetate

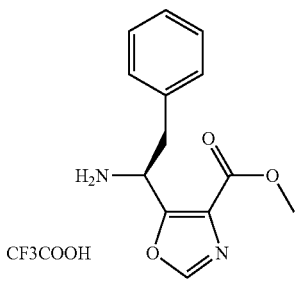

Methyl (S)-5-[1-(tert-butoxycarbonylamino)2-phenylethyl]oxazole-4-carboxylate, (Tett. Lett., 1982, 23, 235; 417 mg) was dissolved in trifluoroacetic acid (3 ml) and stood at ambient temperature for 1 hour and concentrated to give an oil. Trituration with diethyl ether gave the title compound as a white solid. (281 mg).

NMR 3.1–3.25 (1H, m); 3.3–3.4 (1 H, m); 3.7 (3H, s); 5.2–5.3 (1H, m); 7.05(2H,d); 7.2–7.3 (3H, m); 8.7 (1H, s); 8.75–8.85 (3H, bs)

What is claimed is:

1. A compound of formula (1):

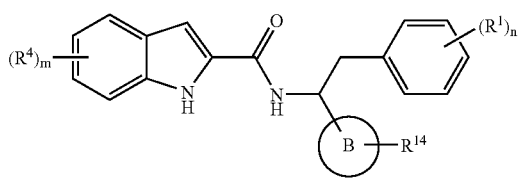

wherein:

n is 0, 1, or 2;

m is 0, 1, or 2;

$R^1$ is independently selected from hydrogen, halo, nitro, cyano, hydroxy, amino, carboxy, carbamoyl, N-$C_{1-4}$alkylcarbamoyl, N,N-($C_{1-4}$alkyl)$_2$carbamoyl, sulphamoyl, N-$C_{1-4}$alkylsulphamoyl, N,N-($C_{1-4}$alkyl)$_2$sulphamoyl, $C_{1-4}$alkyl, $C_{2-4}$alkenyl, $C_{2-4}$alkynyl, $C_{1-4}$alkoxy, $C_{1-4}$alkanoyl, $C_{1-4}$alkanoyloxy, N-($C_{1-4}$alkyl)amino, N,N-($C_{1-4}$alkyl)$_2$amino, hydroxy$C_{1-4}$alkyl, fluoromethyl, difluoromethyl, trifluoromethyl, trifluoromethoxy, and groups of the formula A or A':

(A)

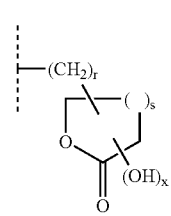

(A')

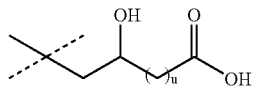

wherein x is 0 or 1, r is 0, 1, 2, or 3, s is 1 or 2 and u is 1 or 2; provided that the hydroxy group is not a substituent on the ring carbon adjacent to the ring oxygen;

$R^4$ is independently selected from hydrogen or halo, B is phenyl $R^{14}$ is selected from hydrogen, halo, $C_{1-4}$alkyl (optionally substituted with 1 or 2 hydroxy groups), $C_{5-7}$cycloalkyl (optionally substituted with 1 or 2 hydroxy groups), $C_{1-4}$alkoxy, cyano, cyano($C_{1-4}$)alkyl, —$COR^3$, ($R^2$)($R^3$)NCO—, and ($R^2$)($R^3$)NSO$_2$—;

$R^2$ and $R^3$ are independently selected from $C_{5-7}$cycloalkyl (optionally substituted with 1 or 2 hydroxy groups), cyano($C_{1-4}$)alkyl, 5- and 6-membered cyclic acetals and mono- and di-methyl derivatives thereof, tetrahydrothiopyranyl, 1-oxotetrahydrothiopyranyl, 1,1-dioxotetrahydrothopyranyl, fluoromethylcarbonyl, difluoromethylcarbonyl, trifluoromethylcarbonyl, $C_{1-4}$alkyl (optionally substituted with 1 or 2 $R^8$ groups), —$OR^8$, and $R^8$;

$R^8$ is independently selected from hydrogen, 2,2-dimethyl-1,3-dioxolan-4-yl, heterocyclyl (optionally substituted on ring carbon or ring nitrogen with 1 or 2 groups selected from hydrogen, nitro, halo, cyano, hydroxy, and $C_{1-4}$alkyl), (heterocyclyl)$C_{1-4}$alkyl (wherein the heterocyclyl is optionally substituted on ring carbon or ring nitrogen with 1 or 2 groups selected from hydrogen, nitro, halo, cyano, hydroxy, and $C_{1-4}$alkyl), aryl (optionally substituted with 1 or 2 groups selected from nitro, halo, cyano, hydroxy, and $C_{1-4}$alkyl), $C_{1-4}$alkyl, $C_{2-4}$alkenyl, cyclo($C_{3-8}$)alkyl, $C_{1-4}$alkoxy, cyano($C_{1-4}$alkyl, amino($C^{1-4}$alkyl (optionally substituted on nitrogen with 1 or 2 groups selected from hydrogen, $C_{1-4}$alkyl, hydroxy, hydroxy($C_{1-4}$alkyl, dihydroxy($C_{1-4}$alkyl, aryl and aryl($C_{1-4}$alkyl), $C_{1-4}$alkylS(O)$_c$($C_{1-4}$alkyl (wherein c is 0, 1 or 2), —N(OH)CHO, —CH$_2$CH(CO$_2$R$^9$)N(R$^9$R$^{10}$), —CH$_2$OR$^9$, (R$^9$)(R$^{10}$)N—, —COOR$^9$, —CH$_2$COOR$^9$, —CH$_2$CONR$^9$R$^{10}$, and —(CH$_2$)$_u$CH(NR$^9$R$^{10}$)CO$_2$R$^9$ (wherein u is 1, 2, or 3);

$R^9$ and $R^{10}$ are independently selected from hydrogen, hydroxy, $C_{1-4}$alkyl (optionally substituted with 1 or 2 hydroxy groups), $C_{5-7}$cycloalkyl (optionally substituted with 1 or 2 hydroxy groups), $C_{2-4}$alkenyl, cyano($C_{1-4}$)alkyl, tetrahydrothiopyranyl, 1-oxotetrahydrothiopyranyl, 1,1-dioxotetrahydrothiopyranyl, 2,2-dimethyl-1,3-dioxolan-4-yl, aryl (optionally substituted with 1 or 2 substituents selected from hydrogen, nitro, halo, hydroxy, and $C_{1-4}$alkyl), and $C_{1-4}$alkyl substituted with $R^{13}$; or $R^9$ and $R^{10}$ together with the nitrogen to which they are attached form a 4- to 6-membered ring where the ring is optionally substituted on carbon with 1 or 2 substituents selected from oxo, hydroxy, carboxy, halo, nitro, nitroso, cyano, isocyano, amino, N-$C_{1-4}$alkylamino, N,N-($C_{1-4}$alkyl)$_2$ amino, carbonyl, $C_{1-4}$alkoxy, heterocyclyl, $C_{1-4}$alkanoyl, $C_{1-4}$alkylS(O)$_f$($C_{1-4}$)alkyl (wherein f is 0, 1, or 2), —N(OH)CHO, (R$^{11}$)(R$^{12}$)NCO—, (R$^{11}$)(R$^{12}$)NSO$_2$—, —COCH$_2$OR$^{11}$, and (R$^{11}$)(R$^{12}$)N—;

$R^{13}$ is selected from hydroxy, $C_{1-4}$alkoxy, heterocyclyl, $C_{1-4}$alkanoyl, $C_{1-4}$alkylS(O)$_d$ (wherein d is 0, 1, or 2), —N(OH)CHO, —C(O)N(R$^{11}$)(R$^{12}$), (R$^{11}$)(R$^{12}$)NSO$_2$—, —COCH$_2$OR$^{11}$, and (R$^{11}$)(R$^{12}$)N—; and R$^{11}$ and R$^{12}$ are independently selected from hydrogen, $C_{1-4}$alkyl, $C_{1-4}$alkoxy, hydroxy$C_{1-4}$alkyl, and $C_{1-4}$alkylS(O)$_e$ (wherein e is 0, 1, or 2); or a pharmaceutically acceptable salt or prodrug thereof.

2. A compound of claim 1 wherein:
   n is 1 or 2;
   $R^1$ is independently selected from hydrogen, halo, nitro, hydroxy, $C_{1-4}$alkyl, or $R^1$ is of the formula A or A':

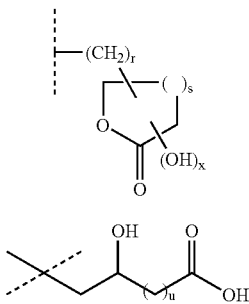

wherein x is 0 or 1, r is 0, 1, 2, or 3, s is 1 or 2 and u is 1 or 2; provided that the hydroxy group is not a substituent on the ring carbon adjacent to the ring oxygen;

B is phenyl;

$R^{14}$ is selected from $C_4$alkyl, cyano($C_{1-4}$)alkyl, —COR$^3$, $(R^2)(R^3)$NCO—, and $(R^2)(R^3)$NSO$_2$;

$R^2$ and $R^3$ are independently selected from $C_{1-4}$alkyl, $C_{1-4}$alkyl (substituted with $R^8$), —OR$^8$, and $R^8$;

$R^8$ is independently selected from hydrogen, heterocyclyl (optionally substituted on carbon or nitrogen with 1 or 2 groups selected from nitro, halo, hydroxy, cyano, and $C_{1-4}$alkyl), (heterocyclyl)($C_{1-4}$alkyl (optionally substituted on carbon or nitrogen with 1 or 2 groups selected from nitro, halo, hydroxy, cyano, and $C_{1-4}$alkyl), aryl (optionally substituted with 1 or 2 groups selected from nitro, halo, cyano, hydroxy, and $C_{1-4}$alkyl), $C_{1-4}$alkyl, $C_{2-4}$alkenyl, cyclo($C_{3-8}$)alkyl, $C_{1-4}$alkoxy, cyano($C_{1-4}$ alkyl, amino($C_{1-4}$alkyl (optionally substituted on nitrogen with 1 or 2 groups selected from hydrogen, $C_{1-4}$alkyl, hydroxy, hydroxy($C_{1-4}$alkyl, dihydroxy($C_{1-4}$ alkyl, aryl, and aryl($C_{14}$alkyl), $C_{1-4}$alkylS(O)$_c$($C_{1-4}$ alkyl (wherein c is 0, 1, or 2), —(CH$^2$)$_u$CO(C0$_2$R$^9$)N $(R^9R^{10})$ (wherein u is 0, 1, or 2), —CH$_2$OR$^9$, $(R^9)$ $(R^{10})$N—, —COOR$^9$, —CH$_2$COOR$^9$,— CH$_2$CONR$^9$R$^{10}$, and —CH$_2$CH$_2$CH(NR$^9$R$^{10}$)CO$_2$R$^9$;

$R^9$ and $R^{10}$ are independently selected from hydrogen, $C_{1-4}$alkyl (optionally substituted with 1 or 2 hydroxy groups), $C_{5-7}$cycloalkyl (optionally substituted with 1 or 2 hydroxy groups), $C_{2-4}$alkenyl, cyano($C_{1-4}$alkyl, and phenyl (optionally substituted with 1 or 2 groups selected from nitro, halo, hydroxy, and cyano);

m is 1;

$R^4$ is chloro;

or a pharmaceutically acceptable salt or in-vivo hydrolysable ester thereof.

3. A pharmaceutical composition which comprises a compound of claim 1, or a pharmaceutically acceptable salt or in-vivo hydrolysable ester thereof in association with a pharmaceutically acceptable diluent or carrier.

4. A method for the treatment of type 2 diabetes, insulin resistance, syndrome X, hyperinsulinaemia, or hyperglucagonaemia in a warm-blooded animal, comprising administering a compound of claim 1, or a pharmaceutically acceptable salt or in-vivo hydrolysable ester thereof.

5. A method for the treatment of type 2 diabetes in a warm-blooded animal, comprising administering a compound of claim 1, or a pharmaceutically acceptable salt or in-vivo hydrolysable ester thereof.

6. A process for the preparation of claim 1, which process comprises: reacting an acid of the formula (2)

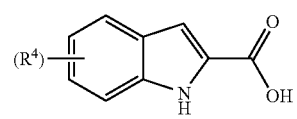

or an activated derivative thereof; with an amine of formula (3)

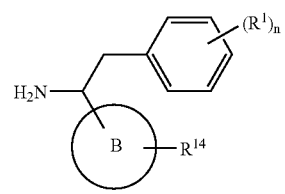

and thereafter if necessary
   i) converting a compound of the formula (1) into another compound of the formula (1);
   ii) removing any protecting groups; or
   iii) forming a pharmaceutically acceptable salt or in-vivo hydrolysable ester.

* * * * *